US00PP29138P2

(12) United States Plant Patent
van Langen

(10) Patent No.: US PP29,138 P2
(45) Date of Patent: Mar. 20, 2018

(54) ***GASTERIA* PLANT NAMED 'AMIAL1622'**

(50) Latin Name: ***Gasteria* hybrid.**
Varietal Denomination: AMIAL1622

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 15/530,591

(22) Filed: Feb. 3, 2017

(51) Int. Cl.
*A01H 5/00* (2006.01)
*A01H 5/12* (2018.01)

(52) U.S. Cl.
USPC ..... Plt./373
CPC ..... *A01H 5/12* (2013.01)

(58) Field of Classification Search
USPC ..... Plt./373, 372
CPC ..... A01H 5/12; A01H 5/02; A01H 5/00
See application file for complete search history.

*Primary Examiner* — Kent L Bell
(74) *Attorney, Agent, or Firm* — Samuel R. McCoy, Jr.

(57) ABSTRACT

A new and distinct *Gasteria* cultivar named 'AMIAL1622' which is characterized by thick succulent foliage arranged in a compact rosette with an erect to arched attitude, near ovate to deltoid foliage that is dark green and moderately to densely covered with near white papillae, as well as the stability of these characteristics from generation to generation.

4 Drawing Sheets

Latin name of the genus and species: The Latin name of the genus and species of the novel variety disclosed herein is *Gasteria* hybrid.

Variety denomination: The inventive variety of *Gasteria* disclosed herein has been given the variety denomination 'AMIAL1622'.

BACKGROUND OF THE INVENTION

Parentage: 'AMIAL1622' is the result of a planned breeding program carried out at a commercial greenhouse in Heerhugowaard, The Netherlands. In the spring of 2013, the inventor performed the controlled intergeneric cross-pollination of the species *Gasteria carinata* (an unnamed plant), the seed parent, with the species *Aloe aristata* (an unnamed plant), the pollen parent. In early 2014, a seedling that exhibited potential commercial value was selected from all other progeny of the same cross. The seedling was given the reference code "16-0098" and allowed to grow to a mature size, for further evaluation to confirm the stability of the characteristics initially observed. In the summer of 2014, the claimed plant was selected for commercialized.

Asexual Reproduction: Asexual reproduction of the new cultivar 'AMIAL1622', by way of rooting leaf cuttings, was first initiated in the summer of 2015 at the inventor's commercial greenhouse in Heerhugowaard, The Netherlands. Through three subsequent generations, the unique features of this cultivar have proven to be stable and true to type.

SUMMARY OF THE INVENTION

The cultivar 'AMIAL1622' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIAL1622'. These characteristics in combination distinguish 'AMIAL1622' as a new and distinct *Gasteria* cultivar:

1. 'AMIAL1622' exhibits thick succulent foliage with an erect to arched attitude, arranged in a compact rosette; and
2. 'AMIAL1622' exhibits large leaves that are near ovate to deltoid in shape, with an apiculate apex; and
3. 'AMIAL1622' exhibits dark green leaves which are moderately covered with white papillae on the adaxial leaf surface and densely covered with near white papillae on the abaxial leaf surface.

BOTANICAL DESCRIPTION OF THE PLANT

Figure 1:
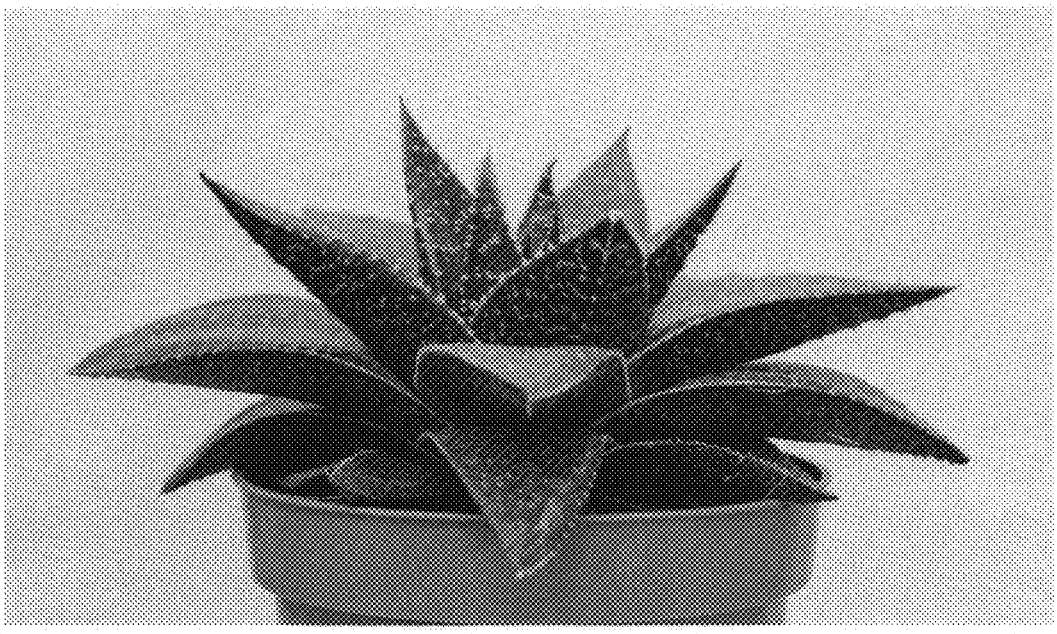
FIG. 1 illustrates, as nearly true as it is reasonably possible to make the same in color photographs of this type, an exemplary plant of 'AMIAL1622' grown in a commercial greenhouse in Heerhugowaard, The Netherlands. This plant is approximately 9 months old, shown planted in a 10.5 cm container.
Figure 2:
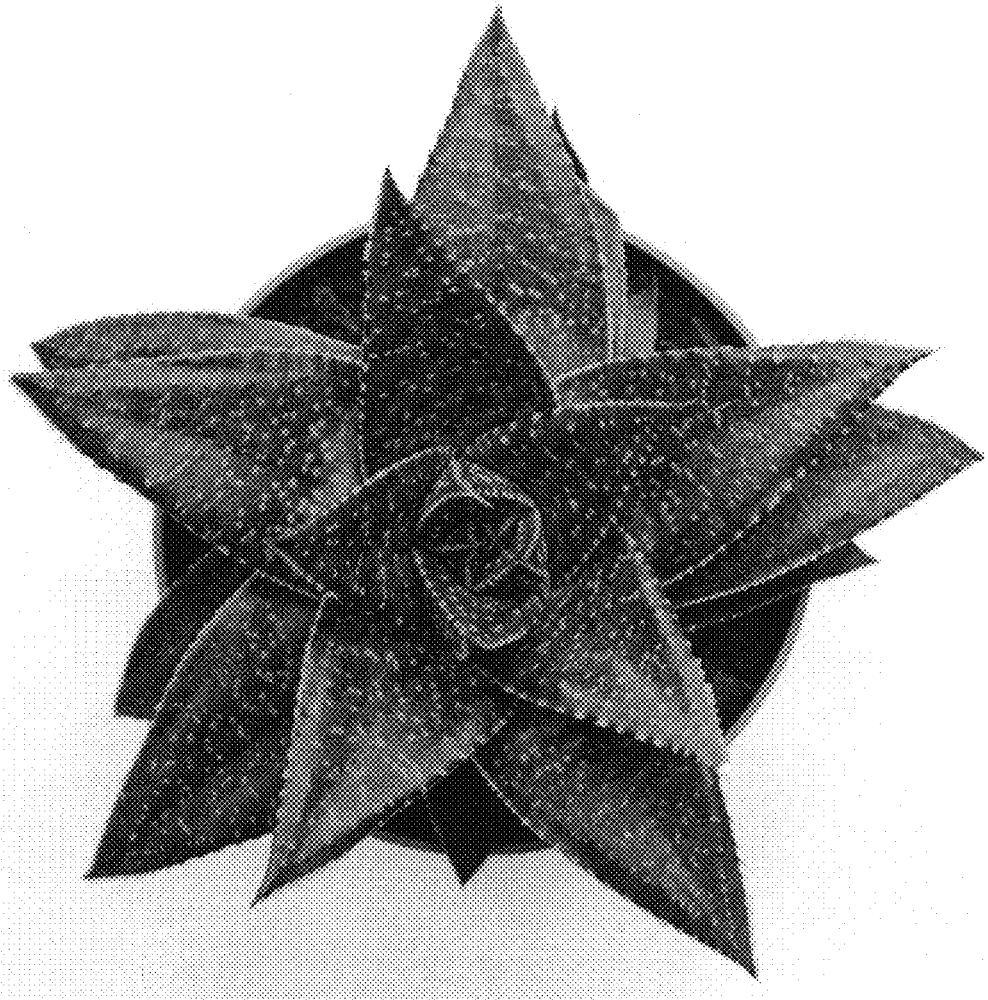
FIG. 2 illustrates, as nearly true as it is reasonably possible to make the same in color photographs of this type, the typical foliage arrangement of 'AMIAL1622'.
Figure 3:
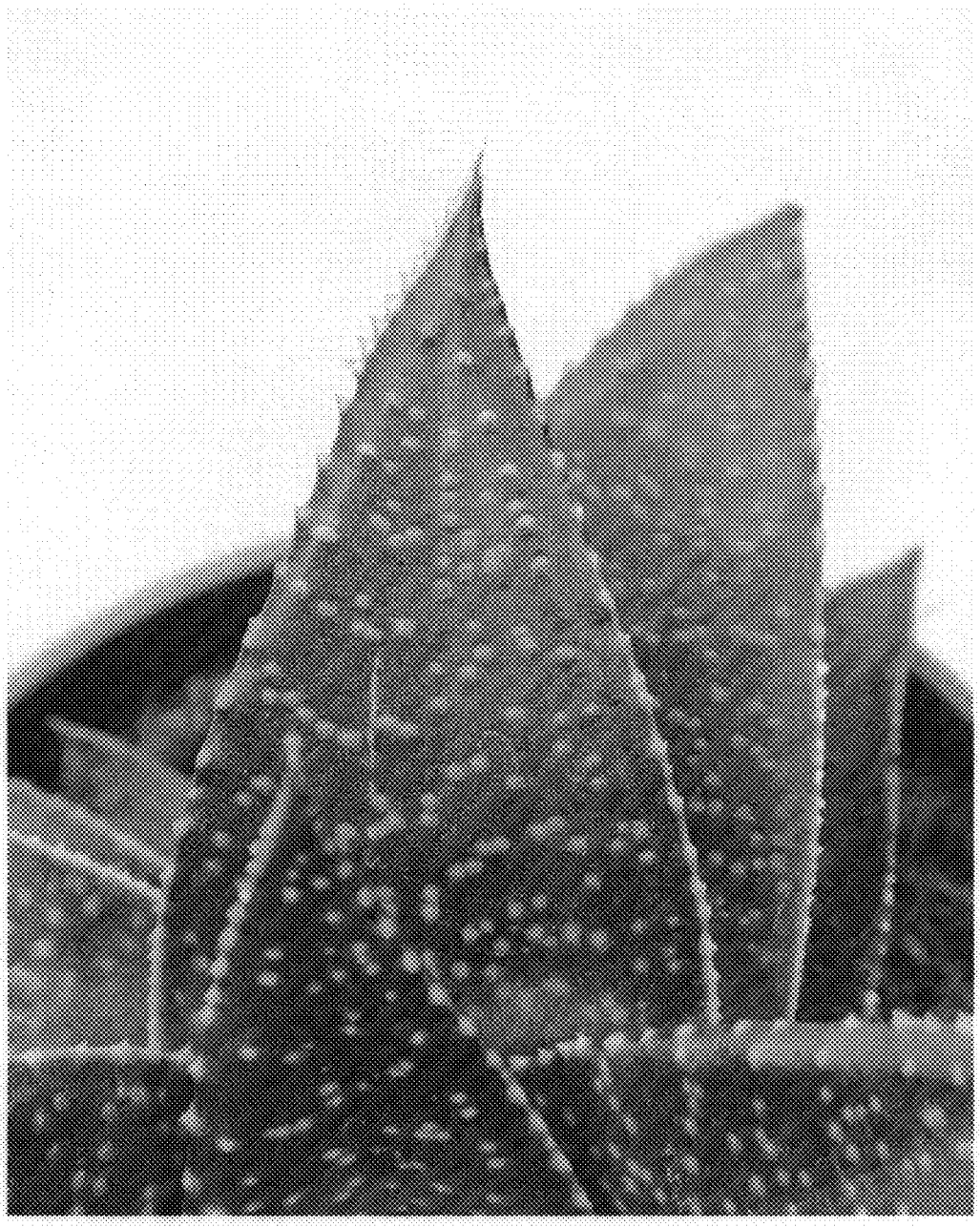
FIG. 3 illustrates, as nearly true as it is reasonably possible to make the same in color photographs of this type, the adaxial surface of the mature foliage 'AMIAL1622'.
Figure 4:
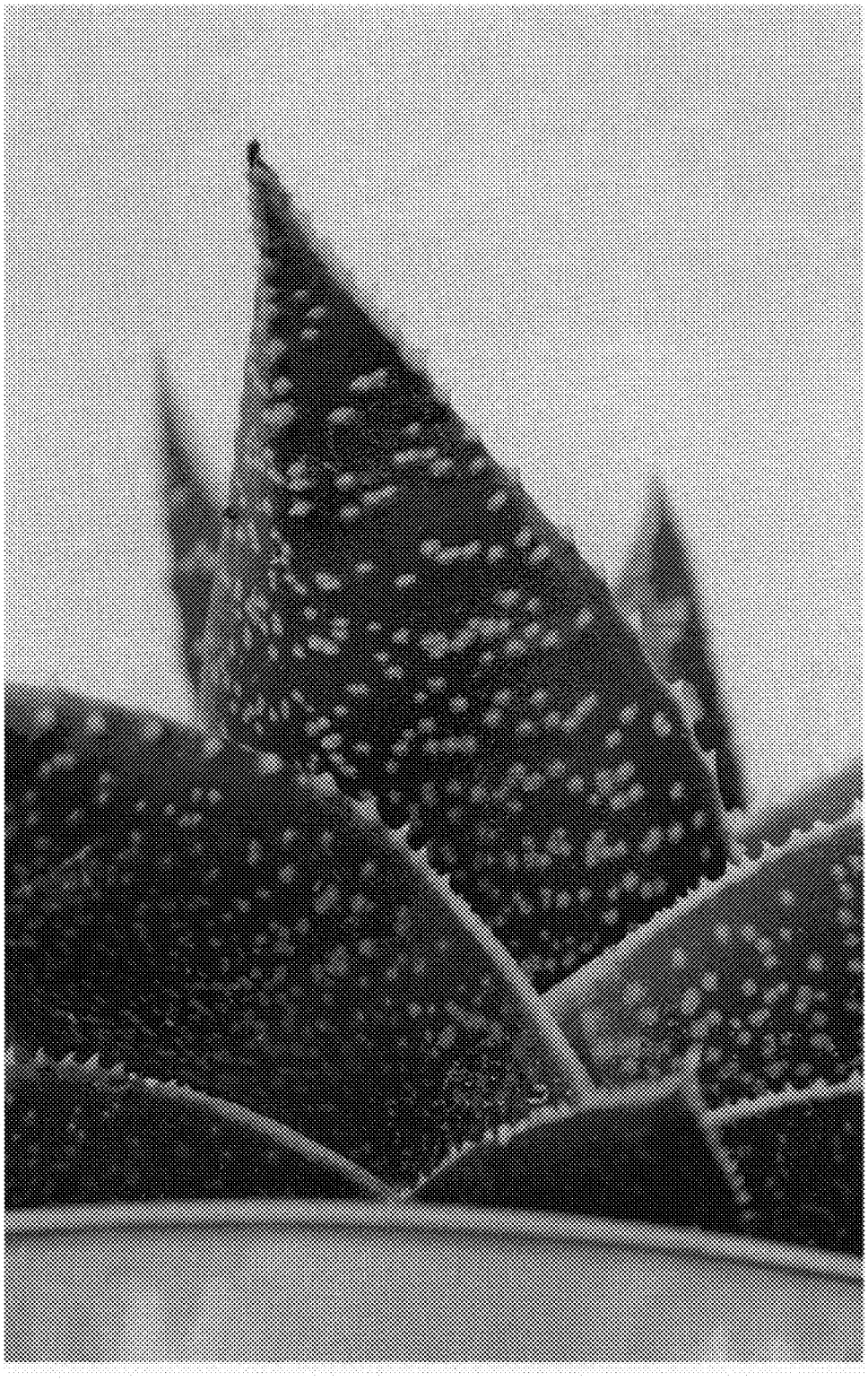
FIG. 4 illustrates, as nearly true as it is reasonably possible to make the same in color photographs of this type, the abaxial surface of the mature foliage 'AMIAL1622'.

The following observations and measurements made in January of 2017 describe averages from a sample set of six specimens of 9 months old 'AMIAL1622' plants grown in 10 cm nursery containers at commercial greenhouse in Heerhugowaard, The Netherlands. Plants were produced using conventional greenhouse production protocols for *Gasteria* which consisted of minimal irrigation and fertilizer applications, and chemical pest and disease control measures against mealy bug and *Botrytis* as required. Plants were grown under approximately 50 percent shade and no photoperiodic treatments or artificial light was given to the plants.

Those skilled in the art will appreciate that certain characteristics will vary with older or, conversely, with younger plants. 'AMIAL1622' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIAL1622' and a comparison with the parents which is the closest known comparator is provided below.

Plant description:

*Growth habit*.—Succulent perennial with foliage growing in a non-branched basal rosette.

*Plant shape*.—Flattened globular.

*Height from soil level to top of foliar plane*.—8.0 cm.

*Plant spread*.—Average of 15.3 cm.

*Growth rate*.—Low.

*Plant vigor*.—Low to moderate.

*Propagation*.—Type — Leaf cuttings. Time to initiate rooting — Approximately 28 to 35 days at approximately 18 degrees Celsius. Crop time — Approximately 15 to 20 weeks to produce a marketable plant in a 7 cm container.

*Disease and pest resistance or susceptibility*.—Neither resistance nor susceptibility to typical *Gasteria* pests and diseases has been observed.

*Environmental tolerances*.—Adapt to, at least, USDA Zones 10 to 12 and temperatures as high as 40 degrees Celsius; low tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 24 leaves per rosette.

*Shape*.—Thick, succulent leaves which are near ovate to deltoid.

*Dimensions*.—7.9 cm long, 3.8 cm wide, and 1.4 cm thick, on average.

*Aspect*.—Very slightly concave.

*Attitude*.—Erect to arched; juvenile foliage is more erect while mature foliage is arched.

*Apex*.—Apiculate.

*Base*.—Broad cuneate.

*Margin*.—Dentate; not undulated.

*Texture, adaxial surface*.—Glabrous and moderately covered with orbicular papillae, each approximately 1.0 mm high and 1.0 mm in diameter.

*Texture, abaxial surface*.—Glabrous and densely covered with orbicular to slightly oblong papillae, each approximately 1.0 mm high and 1.0 mm in diameter.

*Luster, adaxial surface*.—Slightly to moderately glossy.

*Luster, abaxial surface*.—Slightly glossy.

*Color*.—Juvenile foliage, adaxial surface — Green, nearest to a combination of RHS NN137A and 139A, and fading to yellow-green towards the base, nearest to a combination of RHS 145B and 152B; moderately covered with orbicular papillae that are colored greyed-green, in between RHS 191B and 191C. Juvenile foliage, abaxial surface — Green, nearest to a combination of RHS NN137A and 139A, and fading to yellow-green towards the base, nearest to a combination of RHS 144D and 152B; moderately covered with orbicular papillae that are colored greyed-green, in between RHS 191B and 191C. Mature foliage, adaxial surface — In between yellow-green, nearest to RHS 147A, and greyed-green, darker than RHS N189A; colored lighter at the base, nearest to a combination of RHS 141A, 156A and 197C; moderately covered with orbicular papillae that are colored greyed-green, in between RHS 191B and 191C. Mature foliage, adaxial surface — In between yellow-green, nearest to RHS 147A, and greyed-green, darker than RHS N189A; colored lighter at the base, nearest to a combination of RHS 141A, 156A and 197C; densely covered with orbicular papillae that are colored greyed-green, in between RHS 191B and 191C.

*Venation*.—No venation is visible.

*Petiole*.—No petiole; leaves are sessile.

Inflorescence:

No flowering has been observed to date.

Comparisons With the Parent Plants

Plants of the new cultivar 'AMIAL1622' differ from the seed parent an unnamed plant of, *Gasteria carinata*, in the following characteristics described in Table 1 below.

TABLE 1

| Characteristic | 'AMIAL1622' | *Gasteria carinata* (unnamed plant) |
|---|---|---|
| Arrangement of foliage. | Rosette. | Equitant. |
| Leaf shape. | Near ovate to deltoid. | Ovate to narrow deltoid. |
| Leaf apex. | Apiculate | Acute. |
| Leaf margins | Dentate. | Entire. |
| Quantity of papillae on the foliage. | Fewer than the parent. | More than 'AMIAL1622'. |
| General coloration of the mature foliage. | Appears as a darker shade of green. | Appears as a lighter shade of green. |

Plants of the new cultivar 'AMIAL1622' differ from the pollen parent an unnamed plant of, *Aloe aristata*, in the following characteristics described in Table 2 below.

TABLE 2

| Characteristic | 'AMIAL1622' | *Aloe aristata* (unnamed plant) |
|---|---|---|
| Leaf attitude. | More erect than the parent. | More relaxed than 'AMIAL1622'. |
| Leaf width. | Broader than the parent. | Narrower than 'AMIAL1622'. |
| Leaf thickness. | Thicker than the parent. | Thinner than 'AMIAL1622'. |
| Leaf apex. | Apiculate | Acute. |
| General coloration of the mature foliage. | Appears as dark green. | Appears as a somewhat lighter greyed-green. |

Comparisons With the Closest Known Comparator

Plants of the new cultivar 'AMIAL1622' differ from the commercial plant, *Haworthia limifolia* (unnamed and not patented), a species that is closely related to *Gasteria* and *Aloe*, in the following characteristics described in Table 3 below.

TABLE 3

| Characteristic | 'AMIAL1622' | *Haworthia limifolia* (unnamed plant) |
|---|---|---|
| Leaf margins | Dentate. | Entire. |
| Leaf texture. | Prominent near white papillae, irregularly arranged. | Concolorous transverse ridges. |
| General coloration of the mature foliage. | Appears as a darker shade of green. | Appears as a lighter shade of green. |

That which is claimed is:

1. A new and distinct variety of *Gasteria* plant named 'AMIAL1622', substantially as described and illustrated herein.

* * * * *